(12) United States Patent
Kuroiwa et al.

(10) Patent No.: US 7,193,224 B2
(45) Date of Patent: Mar. 20, 2007

(54) SCANNING MICROSCOPE AND LASER MICROSCOPE

(75) Inventors: Yoshinori Kuroiwa, Kamagaya (JP); Shinichi Tanaka, Yokohamo (JP)

(73) Assignee: Nikon Corporation, Tokyo (JP)

( * ) Notice: Subject to any disclaimer, the term of this patent is extended or adjusted under 35 U.S.C. 154(b) by 37 days.

(21) Appl. No.: 11/200,170

(22) Filed: Aug. 10, 2005

(65) Prior Publication Data
US 2006/0033918 A1 Feb. 16, 2006

(30) Foreign Application Priority Data
Aug. 13, 2004 (JP) .............................. 2004-236100

(51) Int. Cl.
*F21V 9/16* (2006.01)
(52) U.S. Cl. .................................... 250/458.1
(58) Field of Classification Search ............ 250/459.1, 250/461.1, 461.2, 462.1, 458.1
See application file for complete search history.

(56) References Cited

U.S. PATENT DOCUMENTS 4,293,221 A * 10/1981 Kay et al. .................... 356/318
5,053,626 A * 10/1991 Tillotson .................. 250/458.1
2006/0031025 A1* 2/2006 Staton et al. .................. 702/20

FOREIGN PATENT DOCUMENTS

JP         2516115         4/1996

* cited by examiner

*Primary Examiner*—David Porta
*Assistant Examiner*—Marcus Taningco
(74) *Attorney, Agent, or Firm*—Miles & Stockbridge PC (57) ABSTRACT

A scanning microscope includes: a light source; an optical system that irradiates light from the light source onto a sample while two-dimensionally scanning the light, and collects light from the sample; a photo-detector that receives the light from the sample which has been collected by the optical system, and converts the light thus received into a brightness signal; an integrating circuit that integrates the brightness signal from the photo-detector for each pixel; and an image forming circuit that forms an image of the sample based upon the brightness signal of each pixel integrated by the integrating circuit. And the integrating circuit includes a plurality of integrators for integrating the brightness signal from the photo-detector and an adder for adding output signals from the plurality of integrators, and integrates the brightness signal while sequentially switching the plurality of integrators for each of a plurality of periods obtained by dividing a period corresponding to a pixel.

9 Claims, 8 Drawing Sheets

SCANNING MICROSCOPE AND LASER MICROSCOPE

INCORPORATION BY REFERENCE

The disclosures of the following priority application are herein incorporated by reference:

Japanese Patent Application No. 2004-236100 filed Aug. 13, 2004

BACKGROUND OF THE INVENTION

1. Field of the Invention

The present invention relates to a scanning microscope and a laser microscope.

2. Description of the Related Art

In general, laser microscopes have functions of condensing a light flux emitted from a light source, and receiving with a photo-detector fluorescence emitted from a sample irradiated (excited) with the condensed light spot, thereby acquiring image information regarding the sample.

With observation of the sample using such a fluorescence laser scanning microscope, a fluorescence image is preferably acquired using as little irradiated (excitation) light as possible in order to minimize damage to the sample which is to be observed. Accordingly, such a fluorescence laser scanning microscope is designed to have improved detection efficiency, thereby enabling imaging of the sample even in a case of weak fluorescence emitted from the sample.

A conventional method is known in which the output signals from a photo-detector are integrated for amplification thereof, thereby amplifying weak signals from a photo-detector with the highest S/N ratio. In general, with such an integrating circuit, the output signal from each pixel is integrated in order, and the integrated signal is reset after integration, for each cycle of a pixel clock signal (a sampling clock signal) (see Japanese Patent Application No. 2516115).

SUMMARY OF THE INVENTION

With the aforementioned conventional laser microscopes, consecutive integration of the signal from each pixel requires reset time for each cycle of the pixel clock signal. This reduces the improvement of the S/N ratio of the system that is achieved by integration of the signal, since the integration time is reduced due to the reset time.

According to the 1st aspect of the invention, a scanning microscope comprises: a light source; an optical system that irradiates light from the light source onto a sample while two-dimensionally scanning the light, and collects light from the sample; a photo-detector that receives the light from the sample which has been collected by the optical system, and converts the light thus received into a brightness signal; an integrating circuit that integrates the brightness signal from the photo-detector for each pixel; and an image forming circuit that forms an image of the sample based upon the brightness signal of each pixel integrated by the integrating circuit. And the integrating circuit includes a plurality of integrators for integrating the brightness signal from the photo-detector and an adder for adding output signals from the plurality of integrators, and integrates the brightness signal while sequentially switching the plurality of integrators for each of a plurality of periods obtained by dividing a period corresponding to a pixel.

According to the 2nd aspect of the invention, in the scanning microscope according to the 1st aspect, it is preferred that integrating periods of the integrators overlap with each other.

According to the 3rd aspect of the invention, in the scanning microscope according to the 1st aspect, it is preferred that the adder is a digital adder.

According to the 4th aspect of the invention, in the scanning microscope according to the 1st aspect, it is preferred that the light from the sample is fluorescence or reflected light from the sample.

According to the 5th aspect of the invention, in the scanning microscope according to the 1st aspect, it is preferred that each of the plurality of integrators is reset after each integrating period thereof.

According to the 6th aspect of the invention, in the scanning microscope according to the 5th aspect, it is preferred that integrating periods of the integrators overlap with each other.

According to the 7th aspect of the invention, in the scanning microscope according to the 5th aspect, it is preferred that the adder is a digital adder.

According to the 8th aspect of the invention, a scanning microscope comprises: a light source that irradiates laser light onto a sample; an optical system that two-dimensionally scans the laser light on the sample, and collects fluorescence or reflected light emitted or reflected from the sample; a photo-detector that receives the fluorescence or the reflected light which has been collected by the optical system, and converts the light thus received into a photoelectric signal; an integrating circuit that integrates the photoelectric signal from the photo-detector for each pixel of an image of the sample; and an image forming circuit that forms an image of the sample based upon the photoelectric signal thus integrated by the integrating circuit. And the integrating circuit includes at least two integrators and an adder for adding output signals of the at least two integrators; and the integrating circuit integrates the photoelectric signal over an entire period corresponding to a pixel by setting an integrating period of one integrator in a reset period following an integrating period of another integrator.

According to the 9th aspect of the invention, a scanning microscope comprises: a light source that irradiates laser light onto a sample; an optical system that two-dimensionally scans the laser light on the sample, and collects fluorescence or reflected light emitted or reflected from the sample; a photo-detector that receives the fluorescence or the reflected light which has been collected by the optical system, and converts the light thus received into a photoelectric signal; an integrating circuit that integrates the photoelectric signal from the photo-detector for each pixel of an image of the sample; and an image forming circuit that forms an image of the sample based upon the photoelectric signal thus integrated by the integrating circuit. And the integrating circuit includes two integrators and an adder for adding output signals from the two integrators; a period corresponding to a pixel of the image of the sample is divided into a first period and a second period; and the integrating circuit repeatedly executes processing in which one integrator integrates the photoelectric signal during the first period, processing in which the one integrator is reset during the second period while another integrator integrates the photoelectric signal, and processing in which the one integrator integrates the photoelectric signal during the first period corresponding to a next pixel while the other integrator is reset.

DESCRIPTION OF THE PREFERRED EMBODIMENTS

Figure 1:
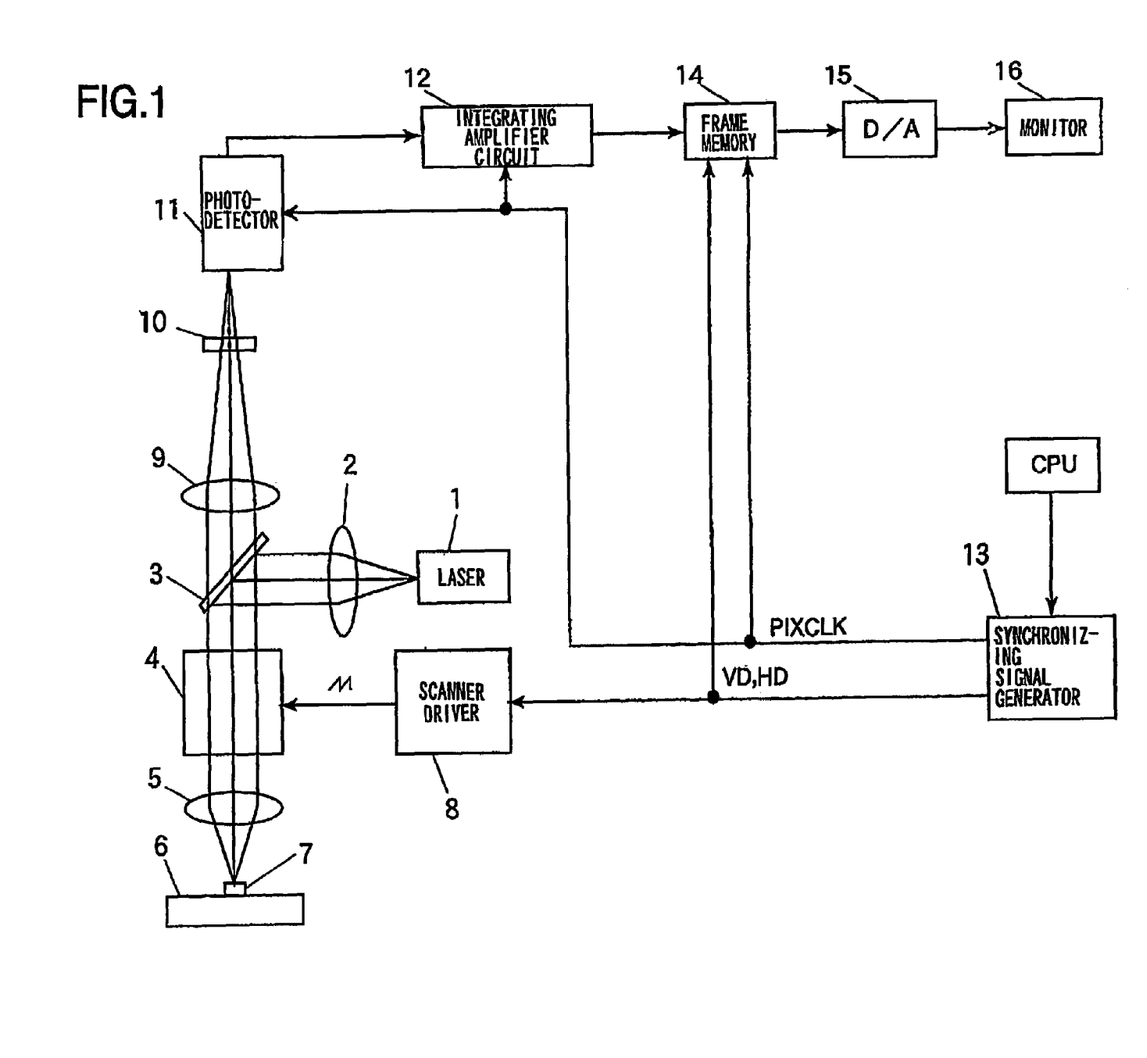
FIG. 1 is a diagram which shows a configuration of a laser microscope according to an embodiment.

FIG. 1 shows a configuration of a scanning laser microscope according to an embodiment. Laser light emitted from a laser light source 1 passes through a collimator lens 2, thereby obtaining a parallel light flux. The parallel light flux thus obtained is reflected by a first dichroic mirror 3, and introduced to a two-dimensional scanning optical system 4. Furthermore, the laser light thus introduced passes through an objective lens 5, thereby forming a light spot on a fluorescent sample (or specimen) 7 mounted on an XY stage 6. Here, the two-dimensional scanning optical system 4 is formed of a pair of Galvano mirror scanners and so on, for example. The two-dimensional scanning optical system 4 having such a configuration has a function of scanning the light spot on the fluorescent sample 7 in the X-Y directions according to driving signals from a scanner driver 8.

Upon irradiating the spot light onto the fluorescent sample 7, fluorescence (or reflected light) is emitted from the fluorescent sample 7. The fluorescence thus emitted is collected by the objective lens 5 and travels along the optical path in the opposite direction in the form of returning light, thereby being introduced into the two-dimensional optical system 4 through the objective lens 5. Furthermore, the light thus introduced is descanned by actions of the two-dimensional scanning optical system 4, and then the light thus descanned is introduced into a condenser lens 9 through the first dichroic mirror 3. The fluorescence thus condensed by the condenser lens 9 is introduced into a fluorescence filter 10 which allows fluorescence of a predetermined wavelength range to pass therethrough. Then, the fluorescence in the predetermined wavelength range is introduced into a photo-detector 11 such as a photo-multiplier tube (PMT), photodiode, or the like, thereby being converted into an electric signal. With the present embodiment, fluorescence is introduced into the photo-detector 11, synchronously with a pixel clock signal PIXCLK output from a synchronizing signal generator 13. The device integrates the signal due to the fluorescence for amplification thereof for each pixel, thereby displaying the signals thus integrated in the form of an image.

The photo-detector 11 outputs a brightness signal due to detected light for each pixel, synchronously with the pixel clock signal PIXCLK output from a synchronizing signal generator 13. The brightness signal from the photo-detector 11 is input to an integrating amplifier circuit 12. The brightness signal thus input is integrated for amplification thereof and is converted into a digital signal, synchronously with the pixel clock signal PIXCLK output from a synchronizing signal generator 13. Detail description will be made later regarding the integrating amplifier circuit 12. The brightness data, which has been integrated for amplification thereof and is converted into a digital signal, is stored in frame memory 14, synchronously with a vertical synchronizing signal VD, a horizontal synchronizing signal HD, and the pixel clock signal PIXCLK. With such a configuration, the brightness data is read out from the frame memory 14, and is converted into an analog signal by actions of a D/A converter 15, thereby being displayed on a monitor 16 in the form of an image.

Figure 2:
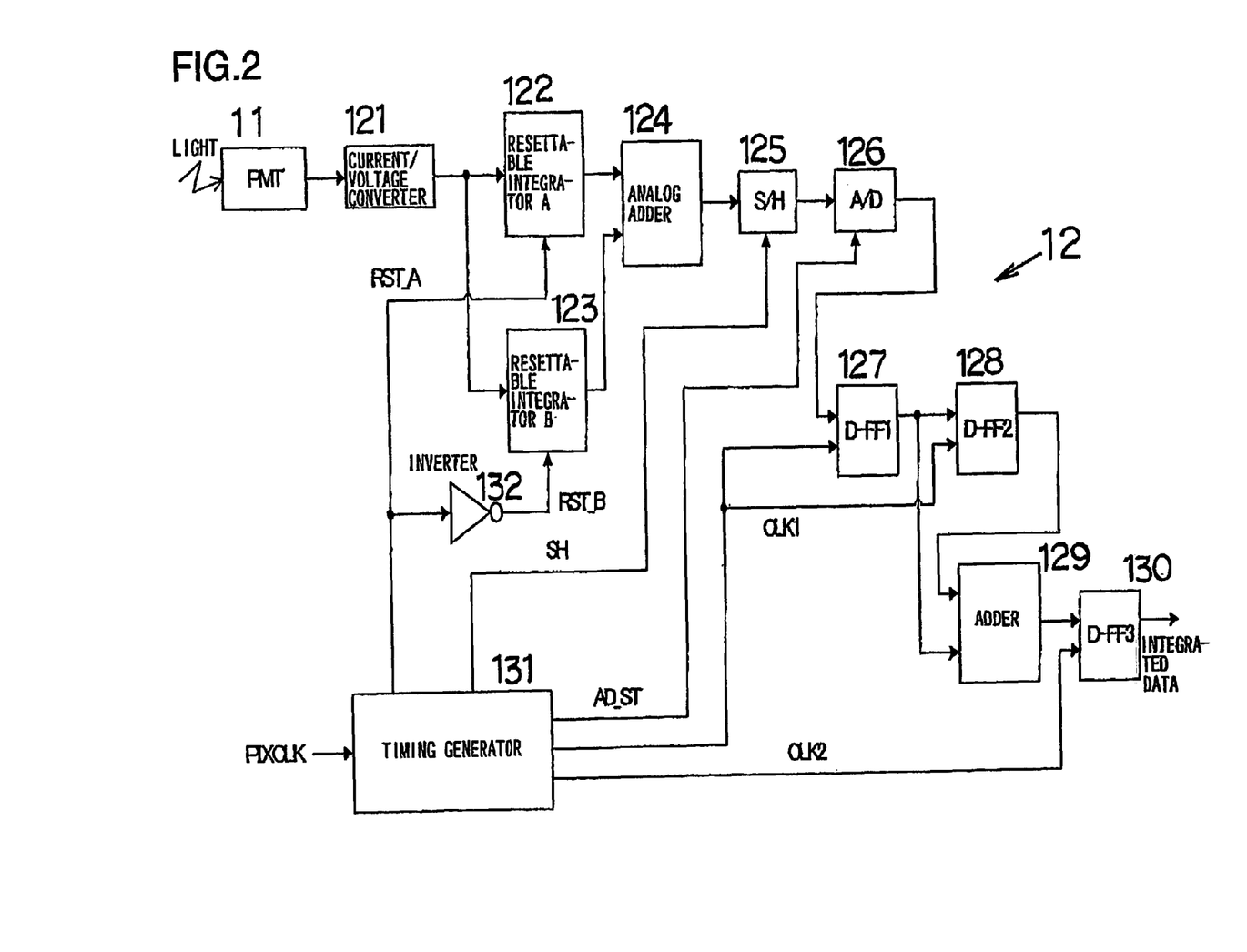
FIG. 2 is a block diagram which shows a detailed configuration of an integrating amplifier circuit according to the embodiment.
Figure 3:
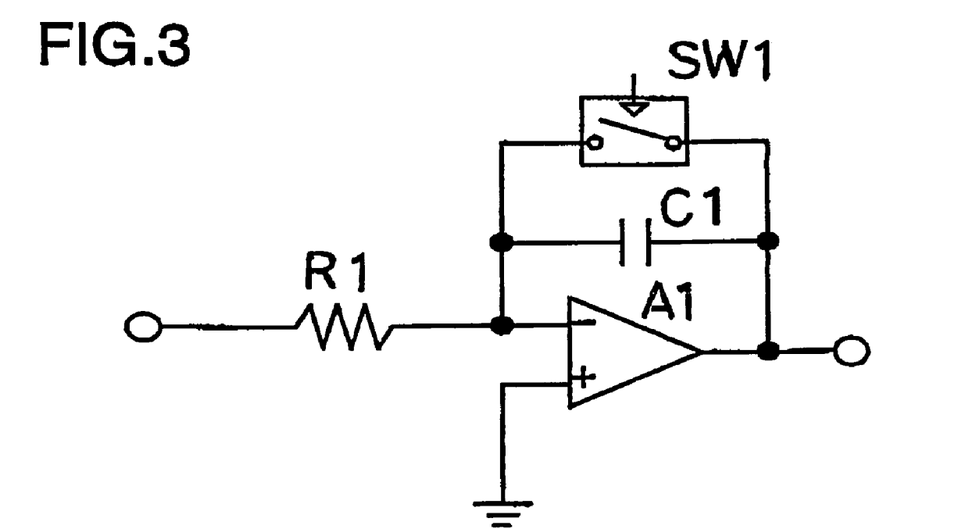
FIG. 3 is a detailed circuit diagram of a resettable integrator according to the embodiment.

FIG. 2 is a detailed circuit diagram of the integrating amplifier circuit 12. The current signal input from the photo-detector 11 is converted into a voltage signal by actions of a current/voltage converter 121, and is input to a resettable integrator A 122 and a resettable integrator B 123 as shown in FIG. 3, for example. Each of the resettable integrators A 122 and B 123 has a configuration in which a reset switch SW1 is connected to both ends of an integrating capacitor C1. With the resettable integrator A 122 having such a configuration, upon reception of a reset signal RSTA (in a case of "H", the resettable integrator A 122 is reset) from a timing generator 131, the switch SW1 is closed, thereby resetting the integrated voltage stored in the capacitor C1 In the same way, with the resettable integrator B 123 having such a configuration, upon reception of a reset signal RSTB (in a case of "H", the resettable integrator B 123 is reset) from a timing generator 131 through an inverter 132, the switch SW1 is closed, thereby resetting the integrated voltage stored in the capacitor C1. Note that the reset signal RSTB is an inverted signal of the reset signal RSTA, inverted by actions of the inverter 132.

Figure 4:
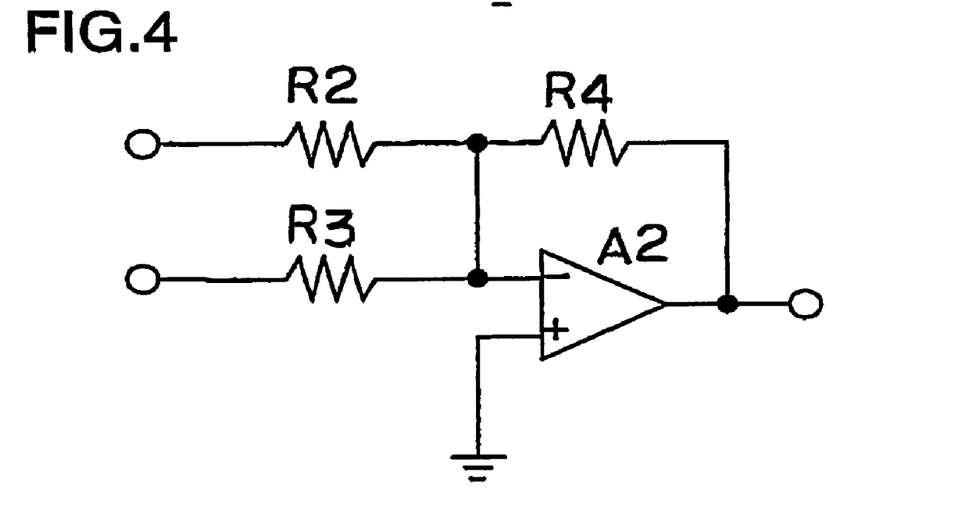
FIG. 4 is a detailed circuit diagram of an analog adder according to the embodiment.

The output signals from the resettable integrators A 122 and B 123 are input to an analog adder 124 having a circuit configuration as shown in FIG. 4, thereby obtaining a summed signal. Furthermore, the summed signal thus output from the analog adder 124 is input to a sample-hold circuit S/H 125, thereby sampling and holding the output signal from the analog adder 124 according to a sample-hold signal SH (in a case of "H", the signal is sampled, and in a case of "L", the signal is held) created by the timing generator 131. The output signal of the sample-hold circuit S/H 125 is input to an A/D converter 126, thereby being converted into digital data according to a conversion start signal ADST (upon detection of the rising edge, A/D conversion is started) received from the timing generator 131.

D flip-flops DFF1 (127) and DFF2 (128) delay the input signal until the rising edge of the clock signal CLK1 received from the timing generator 131. An adder 129 adds the output signals of the D flip-flops DFF1 (127) and DFF2 (128), and outputs the summed signal to a D flip-flops DFF3 (130). The D flip-flops DFF3 (130) delays the input signal until the rising edge of a clock-signal CLK2 received from the timing generator 131. Note that the timing generator 131 creates the reset signals RSTA and RSTB, the sample-hold signal SH, the conversion start signal ADST, and the clock signals CLK1, CLK2, and CLK3, based upon the pixel clock signal PIXCLK received from the synchronizing signal generator 13.

Figure 5:
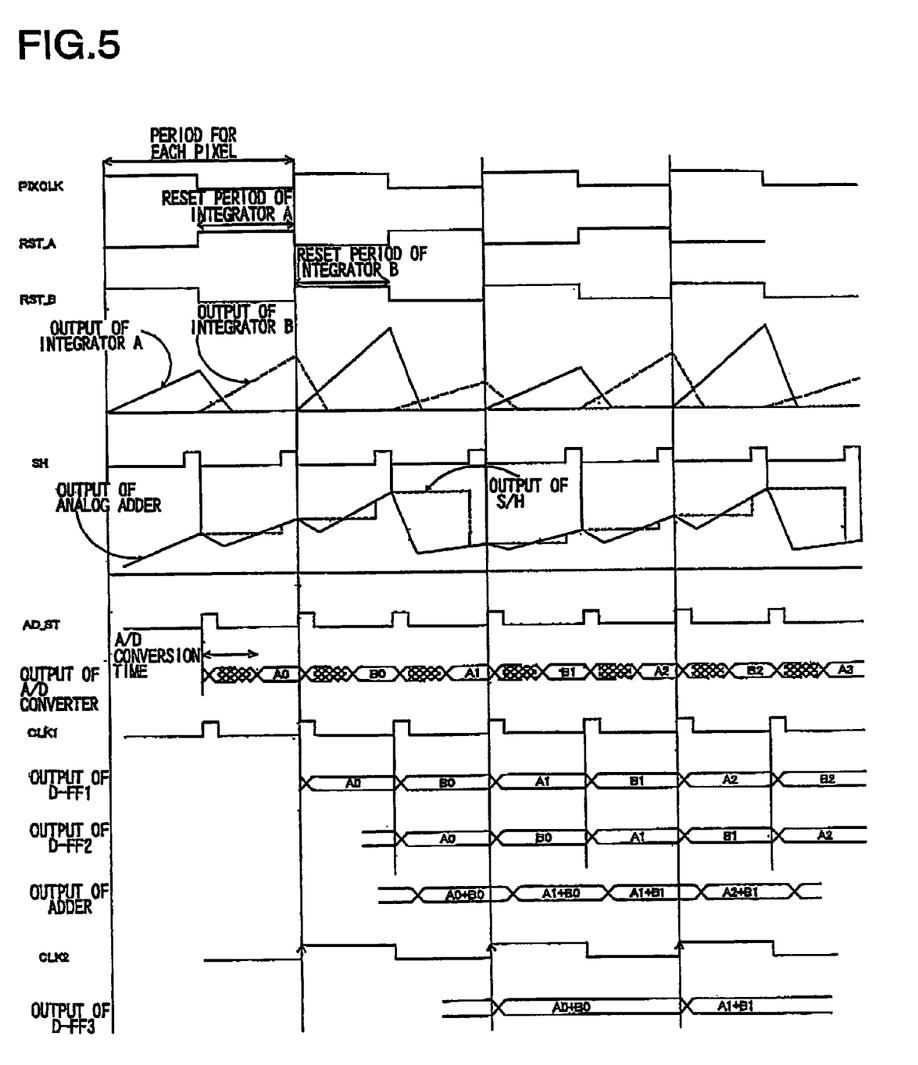
FIG. 5 is a timing chart which shows the operation of the integrating amplifier circuit according to the embodiment.

FIG. 5 shows a timing chart for the operation of the integrating amplifier circuit 12 shown in FIG. 2. While FIG. 5 shows all analog voltage waveforms (output signals from the integrators, analog adder, and so forth) as positive signals for convenience of description, each of the actual output signals from the integrators A 122 and B 123, and the adder 124, shown in FIGS. 3 and 4, is a signal in which a polarity of an input signal is inverted. Furthermore, with the present embodiment, let us say that the A/D converter 126 performs AD conversion for each input signal within half or less the cycle time of the pixel clock signal PIXCLK.

The pixel clock signal PIXCLK is a cyclic signal, wherein the first half cycle is at the "H" level and the latter half cycle is at the "L" level. The integrator A 122 integrates the brightness signal during the "H" period of the pixel clock signal PIXCLK, and is reset during the "L" period thereof. Conversely, the integrator B 123 integrates the brightness signal during the "L" period of the pixel clock signal PIXCLK, and is reset during the "H" period thereof. Note that the integrators A 122 and B 123 each output zero during the reset period thereof. With the present embodiment, the integrators A 122 and B 123 operate with the reset periods being shifted from each other by half the cycle time. With such a configuration, the analog adder 124 adds the output signals of the integrators A 122 and B 123, and the summed signal is input to the sample-hold circuit S/H 125. Thus, the sample-hold circuit S/H 125 alternately detects the output signals from the integrators A 122 and B 123 with the SH signal of "H" level.

The A/D converter 126 performs A/D conversion for the output voltage thus sampled and held by the sample-hold circuit S/H 125 with the rising edge of the A/D start signal ADST as a trigger signal. Now, description will be made with the output signals from the A/D converter 126 as A0, B1, A1, B1, in order of output. That is to say, the first output data integrated by the integrator A 122 for amplification thereof is represented by AD. Then, the subsequent output data of the integrator A 122 is represented by A1, A2, in order of output. In the same way, the first output data integrated by the integrator B 123 for amplification thereof is represented by B0. Then, the subsequent output data of the integrator B 123 is represented by B1, B2, in order of output.

The D flip-flop DFF1 (127) latches the output data of the A/D converter 126 with the rising edge of the clock signal CLK1. On the other hand, the D flip-flop DFF2 (128) latches the output data of the D flip-flop DFF1 (127) with the rising edge of the clock signal CLK1. The adder 129 adds the output signals of the flip-flops DFF1 (127) and DFF2 (128). Furthermore, the D flip-flops DFF3 (130) latches the summed value output from the adder 129 with the rising edge of the clock signal CLK2. As a result, the D flip-flop 3 (130) outputs data sets of (A0+B0), (A1+B1), (A2+B2), in that order, each of which represents the corresponding pixel data, i.e., the integrated brightness data of the corresponding pixel of the photo-detector 11.

As described above, with the present embodiment, the device includes a pair of integrators for integrating the brightness signals output from the photo-detector 11, and an adder for adding the output signals from the pair of the integrators A and B. With such a configuration, the brightness signal is integrated while alternately switching between the integrator A and the integrator B for each period of half the cycle of the pixel clock signal PIXCLK. Specifically, while the integrator A integrates the brightness signal during the first half cycle, the integrator A is reset during the latter half cycle. On the other hand, while the integrator B integrates the brightness signal during the latter half cycle, the integrator B is reset during the first half cycle. The adder adds the output signals of the two integrators A and B for each cycle of the pixel clock signal PIXCLk.

That is to say, one integrator, e.g. the integrator B, integrates the brightness signal during the reset time of the other integrator, e.g. the integrator A, and the reset time of each integrator follows the integrating time thereof. Thus, the brightness signal is integrated over the entire period of each cycle of the pixel clock signal PIXCLK.

In other words, with the present embodiment, the period of each cycle of the pixel clock signal is divided two. While the first period is assigned to the integrating time of the integrator A, the second period is assigned to reset time of the integrator A. Furthermore, the second period is assigned to the integrating time of the integrator B. Furthermore, the next first period following the current second period is assigned to reset time of the integrator B as well as being assigned to the integrating time of the integrator A. With the present embodiment, such an operating sequence is continuously repeated.

This allows integration of the brightness signal output from the photo-detector over the entire period of each cycle of the pixel clock signal PIXCLK without loss of the integrating time due to the reset periods of the integrators A and B. Thus, this maximizes the improved S/N ratio due to integration of the brightness signal, thereby improving the detection efficiency of the fluorescence emitted from the sample.

With the present embodiment as described above, the period of each cycle of the pixel clock signal PIXCLK is divided into two equal periods. The brightness signal is integrated while alternately switching between the integrators A and B for each divided period. Furthermore, the integrators A and B are alternately reset during the corresponding reset time following the integrating time thereof. This allows sufficient reset time of the integrators A and B even in a case of the reduced period of each cycle of the pixel clock signal PIXCLK due to the increased number of pixels.

(Modification)

Figure 6:
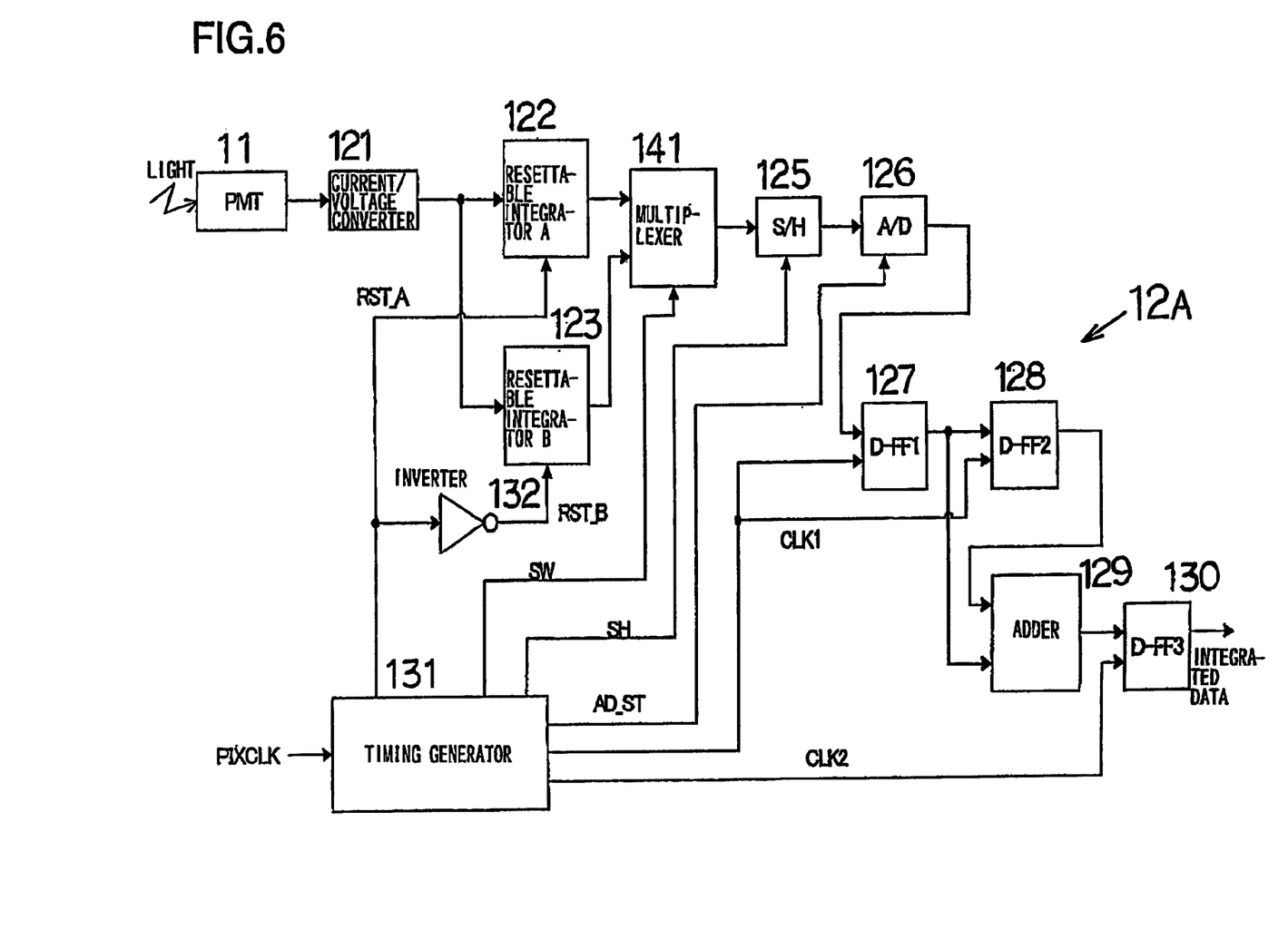
FIG. 6 is a block diagram which shows a detailed configuration of an integrating amplifier circuit according to a modification of the embodiment.
Figure 7:
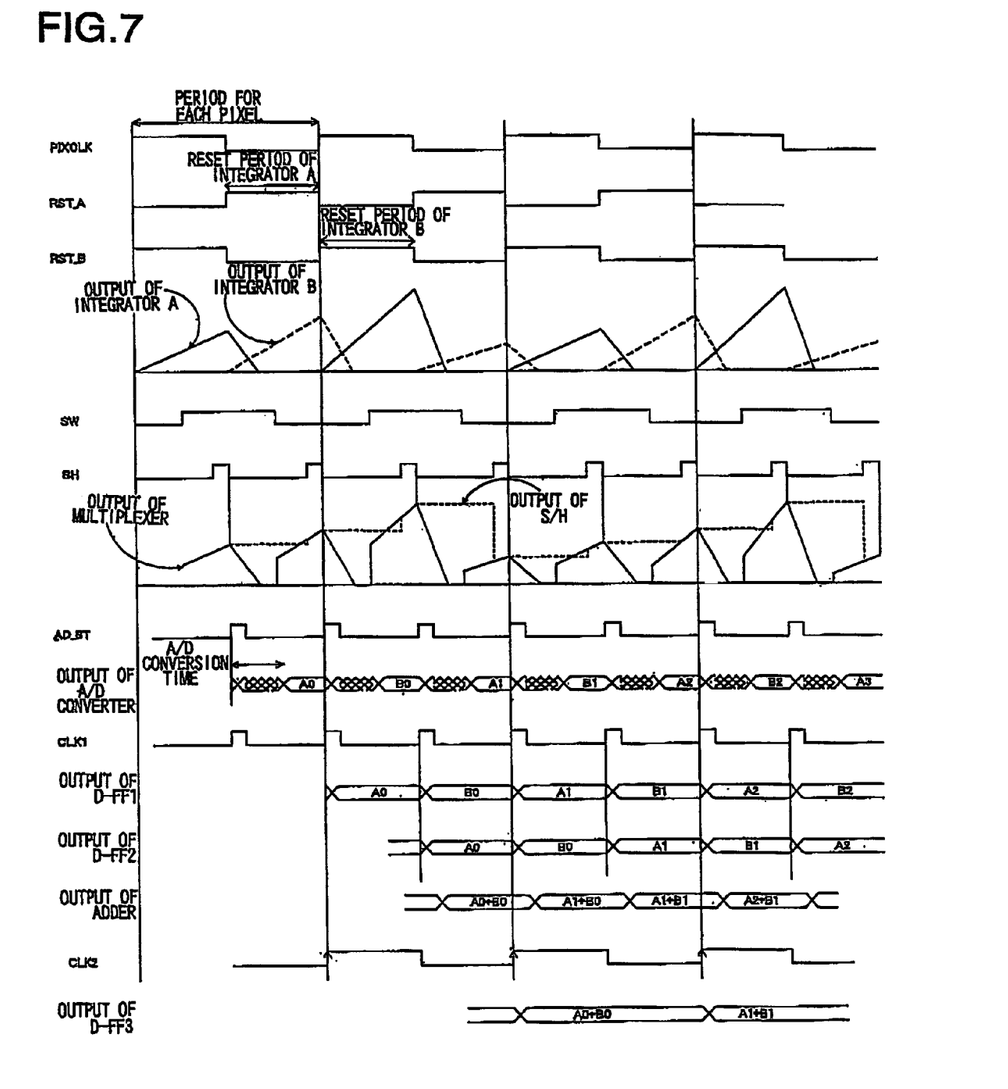
FIG. 7 is a timing chart which shows the operation of the integrating amplifier circuit according to the modification of the embodiment.

FIG. 6 is a detailed circuit diagram of an integrating amplifier circuit 12A according to a modification of the embodiment. FIG. 7 is a timing chart of the operation of the integrating amplifier circuit 12A according to the modification shown in FIG. 6. Note that in FIG. 6, the same components as those shown in FIG. 2 are denoted by the same reference numerals, and description will be mainly made regarding the difference therebetween. The integrating amplifier circuit 12A according to the modification includes a multiplexer 141 instead of the analog adder 124 shown in FIG. 2. The multiplexer 141 switches the output signal between the output signals of the integrators A 122 and B 123 according to a switching signal SW output from the timing generator 131. Specifically, in a case of the switching signal SW of "H", the multiplexer 141 selects the output signal of the integrator A 122. On the other hand, in a case of the switching signal SW of "L", the multiplexer 141 selects the output signal of the integrator B 123. The other operation is the same as that of the integrating amplifier circuit 12 shown in FIG. 2, and accordingly, description thereof will be omitted.

(Another Modification)

Figure 8:
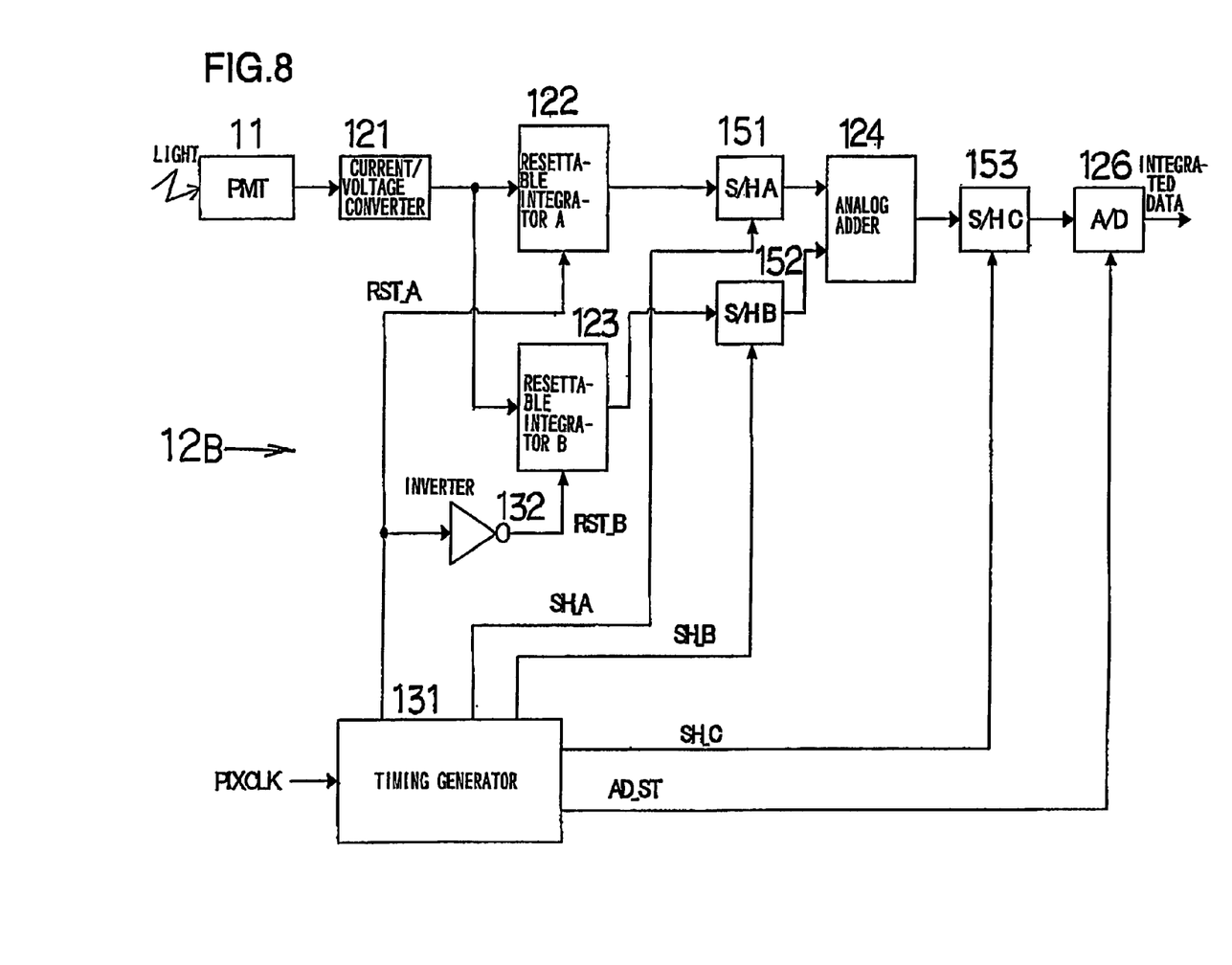
FIG. 8 is a block diagram which shows a detailed configuration of an integrating amplifier circuit according to another modification of the embodiment.
Figure 9:
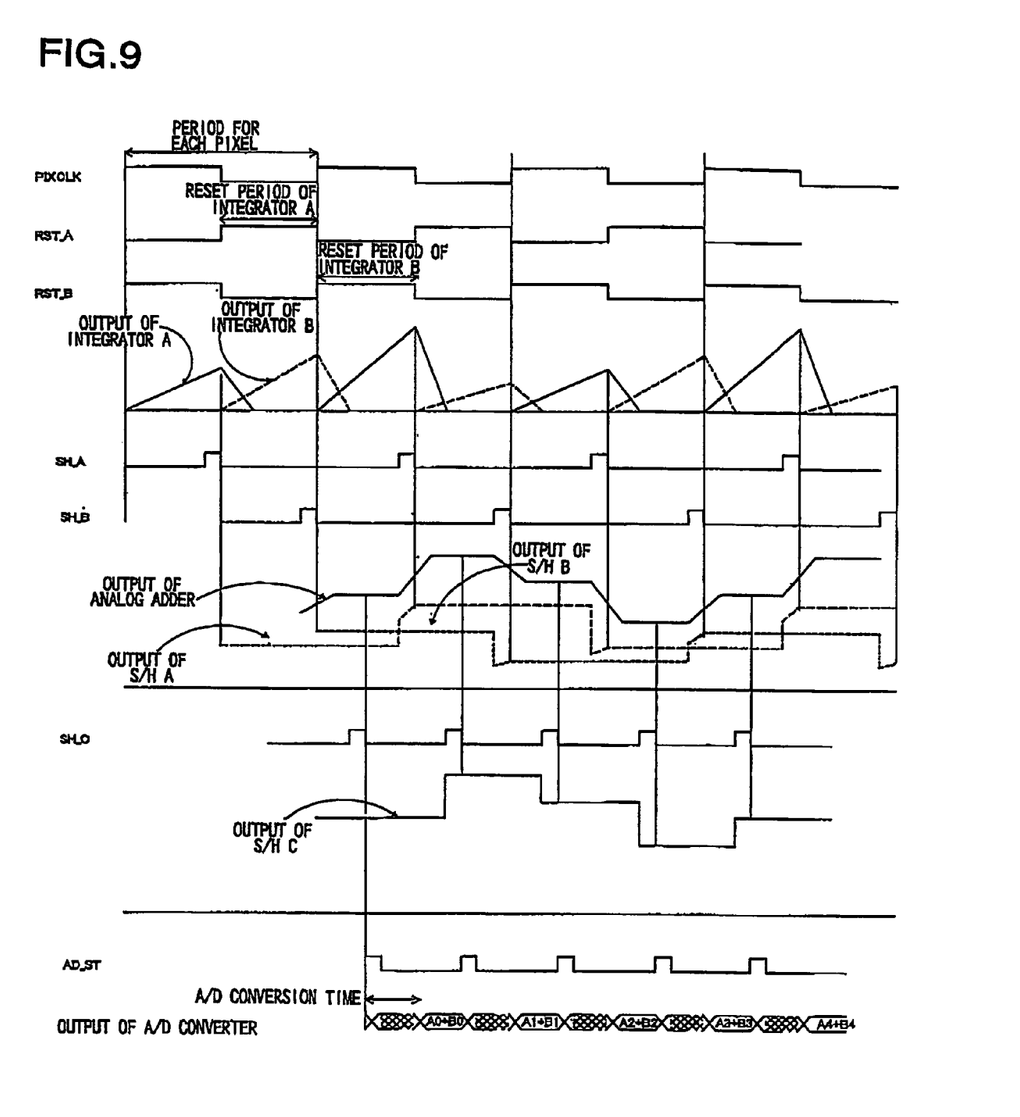
FIG. 9 is a timing chart which shows the operation of the integrating amplifier circuit according to the other modification of the embodiment.

FIG. 8 is a detailed circuit diagram of an integrating amplifier circuit 12B according to another modification of the embodiment. FIG. 9 is a timing chart of the operation of the integrating amplifier circuit 12B according to the aforementioned modification shown in FIG. 8. Note that in FIG. 8, the same components as those shown in FIG. 2 are denoted by the same reference numerals, and description will be mainly made regarding the difference therebetween. Description has been made regarding the integrating amplifier circuit 12 with reference to FIG. 2, in which the output signals from the integrators A 122 and B 123 are each converted into digital signals, and then the digital signals thus converted are added, thereby outputting the summed signal. With the integrating amplifier circuit 12B according to the modification, the output signals from the integrators A 122 and B 123 are sampled and held by the sample-hold circuits S/H A151 and S/H A152, respectively, and then the output signals thus sampled and held are added by the analog adder 124. The summed value thus obtained matches the integrated value in which the pixel value is integrated for each pixel. With the present modification, the sample-hold circuit S/H C153 samples and holds the summed value thus obtained, and the A/D converter 126 performs A/D conversion for the analog value thus sampled and held, thereby obtaining the integrated data for each pixel, i.e., the integrated brightness data of each pixel of the photo-detector 11. The other operation is the same as that of the integrating amplifier circuit 12 shown in FIG. 2, and accordingly, description thereof will be omitted.

A set of the aforementioned collimator lens 2, the first dichroic mirror 3, the two-dimensional scanning optical system 4, the objective lens 5, the scanner driver 8, and the condenser lens 9, may be referred to as "an optical system". Also, each of the integrating amplifier circuits 12, 12A, and 12B, may be simply referred to as "an integrator". Also, a set of the synchronizing signal generator 13, the frame memory 14, and the D/A converter 15 may be referred to as "an image forming circuit".

Description has been made regarding the embodiment and modifications thereof in which the pixel clock signal PIXCLK used therein is a cyclic signal with the first half cycle at the "H" level and with the latter half cycle at the "L" level. With such an arrangement, while the integrator A integrates the brightness signal during the period of "H" of the pixel clock signal PIXCLK, the integrator A is reset during the period of "L". On the other hand, while the integrator B integrates the brightness signal during the period of "L" of the pixel clock signal PIXCLK, the integrator B is reset during the period of "H". Also, an arrangement may be made in which the integrating periods of the integrators A and B overlap with each other in each cycle of the pixel clock signal PIXCLK.

Also, the present invention is not restricted to an arrangement in which the integrators A and B operate with the same integrating periods and the same reset periods as equal parts into which the period of one cycle of the pixel clock signal is divided. Rather, an arrangement maybe made in which the integrators A and B operate with integrating periods and reset periods which are different from one another.

While description has been made regarding an arrangement employing the two integrators A and B, an arrangement may be made employing three or more integrators. Specifically, the device may include three or more integrators for integrating the brightness signal received from the photo-detector, and an adder for adding the output signals of the three or more integrators. With such a configuration, the device integrates the brightness signal while alternately switching between the integrators, thereby integrating the brightness signal over three or more divided periods forming the entire period of each cycle of the pixel clock signal PIXCLK. Furthermore, the integrators are alternately reset during the next period following the integrating period. Thus, the adder adds the output signals of the integrators over the entire period of each cycle of the pixel clock signal PIXCLK.

While description has been made in the aforementioned embodiment regarding an arrangement in which the present invention is applied to a fluorescence laser scanning microscope, the present invention is not restricted to the fluorescence laser scanning microscope, and may also be applied to a spectral detector including photo-detectors each of which is prepared for a desired wavelength.

The above described embodiments are examples, and various modifications can be made without departing from the spirit and scope of the present invention.

What is claimed is:

1. A scanning microscope comprising:
   a light source;
   an optical system that irradiates light from the light source onto a sample while two-dimensionally scanning the light, and collects light from the sample;
   a photo-detector that receives the light from the sample which has been collected by the optical system, and converts the light thus received into a brightness signal;
   an integrating circuit that integrates the brightness signal from the photo-detector for each pixel; and
   an image forming circuit that forms an image of the sample based upon the brightness signal of each pixel integrated by the integrating circuit, wherein
   the integrating circuit includes a plurality of integrators for integrating the brightness signal from the photo-detector and an adder for adding output signals from the plurality of integrators, and integrates the brightness signal while sequentially switching the plurality of integrators for each of a plurality of periods obtained by dividing a period corresponding to a pixel.

2. A scanning microscope according to claim 1, wherein integrating periods of the integrators overlap with each other.

3. A scanning microscope according to claim 1, wherein the adder is a digital adder.

4. A scanning microscope according to claim 1, wherein the light from the sample is fluorescence or reflected light from the sample.

5. A scanning microscope according to claim 1, wherein each of the plurality of integrators is reset after each integrating period thereof.

6. A scanning microscope according to claim 5, wherein integrating periods of the integrators overlap with each other.

7. A scanning microscope according to claim 5, wherein the adder is a digital adder.

8. A scanning microscope comprising:
   a light source that irradiates laser light onto a sample;
   an optical system that two-dimensionally scans the laser light on the sample, and collects fluorescence or reflected light emitted or reflected from the sample;
   a photo-detector that receives the fluorescence or the reflected light which has been collected by the optical system, and converts the light thus received into a photoelectric signal;

an integrating circuit that integrates the photoelectric signal from the photo-detector for each pixel of an image of the sample; and an image forming circuit that forms an image of the sample based upon the photoelectric signal thus integrated by the integrating circuit, wherein:

the integrating circuit includes at least two integrators and an adder for adding output signals of the at least two integrators; and the integrating circuit integrates the photoelectric signal over an entire period corresponding to a pixel by setting an integrating period of one integrator in a reset period following an integrating period of another integrator.

9. A scanning microscope comprising:

a light source that irradiates laser light onto a sample;

an optical system that two-dimensionally scans the laser light on the sample, and collects fluorescence or reflected light emitted or reflected from the sample;

a photo-detector that receives the fluorescence or the reflected light which has been collected by the optical system, and converts the light thus received into a photoelectric signal;

an integrating circuit that integrates the photoelectric signal from the photo-detector for each pixel of an image of the sample; and an image forming circuit that forms an image of the sample based upon the photoelectric signal thus integrated by the integrating circuits wherein:

the integrating circuit includes two integrators and an adder for adding output signals from the two integrators;

a period corresponding to a pixel of the image of the sample is divided into a first period and a second period; and the integrating circuit repeatedly executes processing in which one integrator integrates the photoelectric signal during the first period, processing in which the one integrator is reset during the second period while another integrator integrates the photoelectric signal, and processing in which the one integrator integrates the photoelectric signal during the first period corresponding to a next pixel while the other integrator is reset.

* * * * *